US008430863B2

(12) United States Patent
Webler

(10) Patent No.: US 8,430,863 B2
(45) Date of Patent: Apr. 30, 2013

(54) VISUALIZATION OF A CATHETER VIEWED UNDER ULTRASOUND IMAGING

(75) Inventor: William E. Webler, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1098 days.

(21) Appl. No.: 12/356,159

(22) Filed: Jan. 20, 2009

(65) Prior Publication Data

US 2009/0131910 A1   May 21, 2009

Related U.S. Application Data

(63) Continuation-in-part of application No. 12/044,704, filed on Mar. 7, 2008, now Pat. No. 8,382,674, which is a continuation-in-part of application No. 11/293, 420, filed on Dec. 2, 2005, now Pat. No. 7,867,169.

(51) Int. Cl.
*A61M 25/00* (2006.01)
(52) U.S. Cl.
USPC ............................................ 604/523; 29/594
(58) Field of Classification Search .................. 264/241, 264/248, 250, 319, 327; 29/594
See application file for complete search history.

(56) References Cited

U.S. PATENT DOCUMENTS

| | | |
|---|---|---|
| 3,984,911 A | 10/1976 | Krug et al. |
| 4,052,989 A | 10/1977 | Kline |
| 4,175,266 A | 11/1979 | Nakano et al. |
| 4,234,887 A | 11/1980 | Vanderslice |
| 4,401,124 A | 8/1983 | Guess et al. |
| 4,509,523 A | 4/1985 | Pevsner et al. |
| 4,697,595 A | 10/1987 | Breyer et al. |
| 5,040,537 A | 8/1991 | Katakura |
| 5,045,072 A | 9/1991 | Castillo et al. |
| 5,081,997 A | 1/1992 | Bosley et al. |
| 5,201,314 A | 4/1993 | Bosley, Jr. et al. |
| 5,215,680 A | 6/1993 | D'Arrigo |
| 5,219,401 A | 6/1993 | Cathignol et al. |
| 5,242,429 A | 9/1993 | Nwaneri et al. |
| 5,259,837 A | 11/1993 | Van Wormer |

(Continued)

FOREIGN PATENT DOCUMENTS

| | | |
|---|---|---|
| WO | 9951294 A1 | 10/1999 |
| WO | 2007/067324 A | 6/2007 |

OTHER PUBLICATIONS

International Search Report dated Dec. 20, 2009 from the co-pending International Application No. WO 2009/114340 published on Dec. 3, 2009.

(Continued)

*Primary Examiner* — Unsu Jung
*Assistant Examiner* — Saurel J Selkin
(74) *Attorney, Agent, or Firm* — Fulwider Patton LLP

(57) ABSTRACT

A catheter for use in a patient's body lumen, having a shaft section configured to minimize ultrasonic image artifacts and the direct ultrasonic image brightness of the shaft surface and its internal components, and to produce its image at a wide range of imaging angles, preferably with an intensity not substantially different than surrounding tissue of the body lumen under ultrasound visualization. The shaft section is operative for the desired use of the catheter, yet is also configured to facilitate accurately imaging the shape and location of the shaft section, and easily differentiate it from the surrounding anatomy without unduly obscuring the images of the adjacent anatomy using an ultrasound imaging system.

19 Claims, 4 Drawing Sheets

U.S. PATENT DOCUMENTS

| | | | |
|---|---|---|---|
| 5,275,162 | A | 1/1994 | Edwards et al. |
| 5,289,831 | A | 3/1994 | Bosley et al. |
| 5,491,521 | A | 2/1996 | Boie et al. |
| 5,591,142 | A * | 1/1997 | Van Erp .................. 604/526 |
| 5,704,926 | A | 1/1998 | Sutton et al. |
| 5,738,100 | A | 4/1998 | Yagami et al. |
| 5,820,554 | A | 10/1998 | Davis et al. |
| 5,921,933 | A | 7/1999 | Sarkis et al. |
| 5,967,988 | A | 10/1999 | Briscoe et al. |
| 6,053,870 | A | 4/2000 | Fulton et al. |
| 6,106,473 | A | 8/2000 | Violante et al. |
| 6,123,718 | A | 9/2000 | Tu et al. |
| 6,179,809 | B1 | 1/2001 | Khairkhahan et al. |
| 6,306,094 | B1 | 10/2001 | Joseph |
| 6,315,777 | B1 | 11/2001 | Comben |
| 6,321,109 | B2 | 11/2001 | Ben-Haim et al. |
| 6,358,211 | B1 | 3/2002 | Mamayek |
| 6,366,206 | B1 | 4/2002 | Ishikawa et al. |
| 6,371,915 | B1 | 4/2002 | Koger |
| 6,500,141 | B1 | 12/2002 | Irion et al. |
| 6,528,199 | B1 | 3/2003 | Mercuri et al. |
| 6,575,930 | B1 | 6/2003 | Trombley, III et al. |
| 6,592,580 | B1 | 7/2003 | Stockert et al. |
| 6,610,005 | B1 | 8/2003 | Tao |
| 6,610,016 | B1 | 8/2003 | Violante et al. |
| 6,648,874 | B2 | 11/2003 | Parisi et al. |
| 6,716,166 | B2 | 4/2004 | Govari |
| 6,723,052 | B2 | 4/2004 | Mills |
| 6,743,215 | B2 | 6/2004 | Bernabei |
| 6,749,554 | B1 | 6/2004 | Snow et al. |
| 6,749,624 | B2 | 6/2004 | Knowlton |
| 6,860,856 | B2 | 3/2005 | Ward |
| 6,916,328 | B2 | 7/2005 | Brett |
| 7,065,394 | B2 | 6/2006 | Hobot et al. |
| 7,147,817 | B1 | 12/2006 | Lim et al. |
| 7,229,413 | B2 | 6/2007 | Violante et al. |
| 7,278,991 | B2 | 10/2007 | Morris et al. |
| 7,285,108 | B2 | 10/2007 | Koerner et al. |
| 2003/0009153 | A1 | 1/2003 | Brisken |
| 2003/0014100 | A1 | 1/2003 | Meens et al. |
| 2003/0018293 | A1 | 1/2003 | Tanghoj et al. |
| 2003/0130711 | A1 | 7/2003 | Pearson et al. |
| 2003/0153960 | A1 | 8/2003 | Chornenky et al. |
| 2003/0181928 | A1 | 9/2003 | Vidlund et al. |
| 2004/0019371 | A1 | 1/2004 | Jaafar et al. |
| 2004/0024371 | A1 | 2/2004 | Plicchi et al. |
| 2004/0138712 | A1 | 7/2004 | Tamarkin et al. |
| 2005/0070844 | A1 | 3/2005 | Chow et al. |
| 2005/0146085 | A1 * | 7/2005 | Holman et al. .............. 264/535 |
| 2008/0154136 | A1 | 6/2008 | Webler |

OTHER PUBLICATIONS

Extended European Search Report dated Jul. 5, 2012 in the corresponding European Patent Application No. 12158440.3.
International Search Report dated Mar. 18, 2010 from corresponding International Application No. WO 2010/20235 filed on Jan. 6, 2010.

* cited by examiner

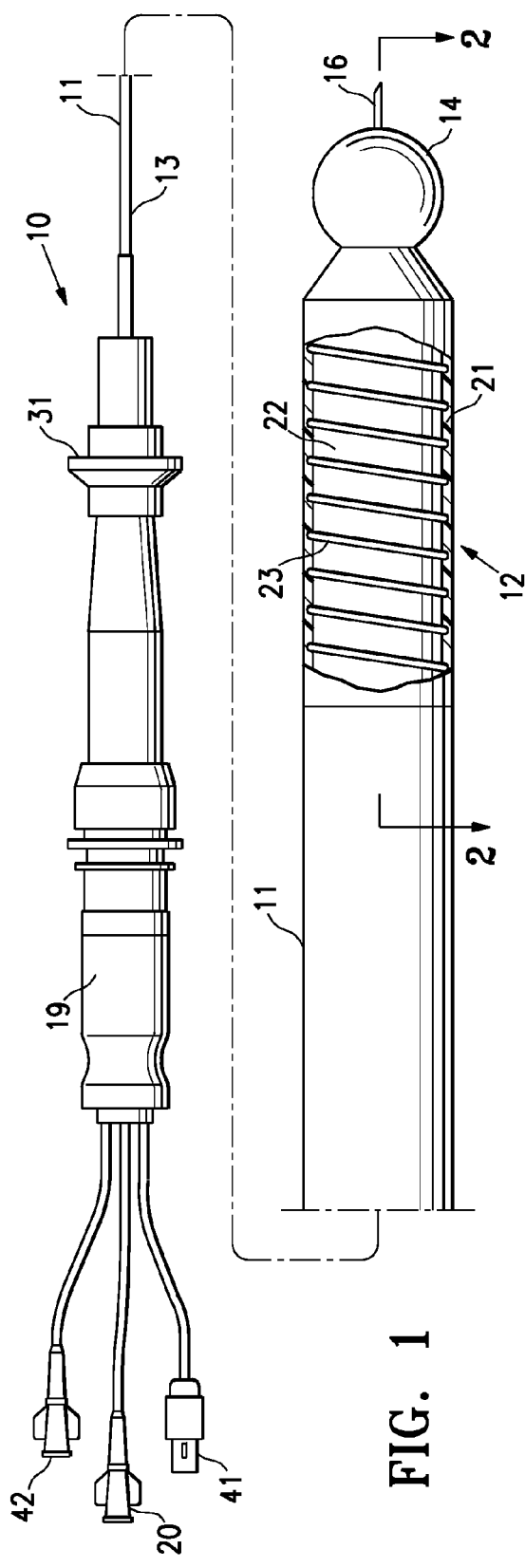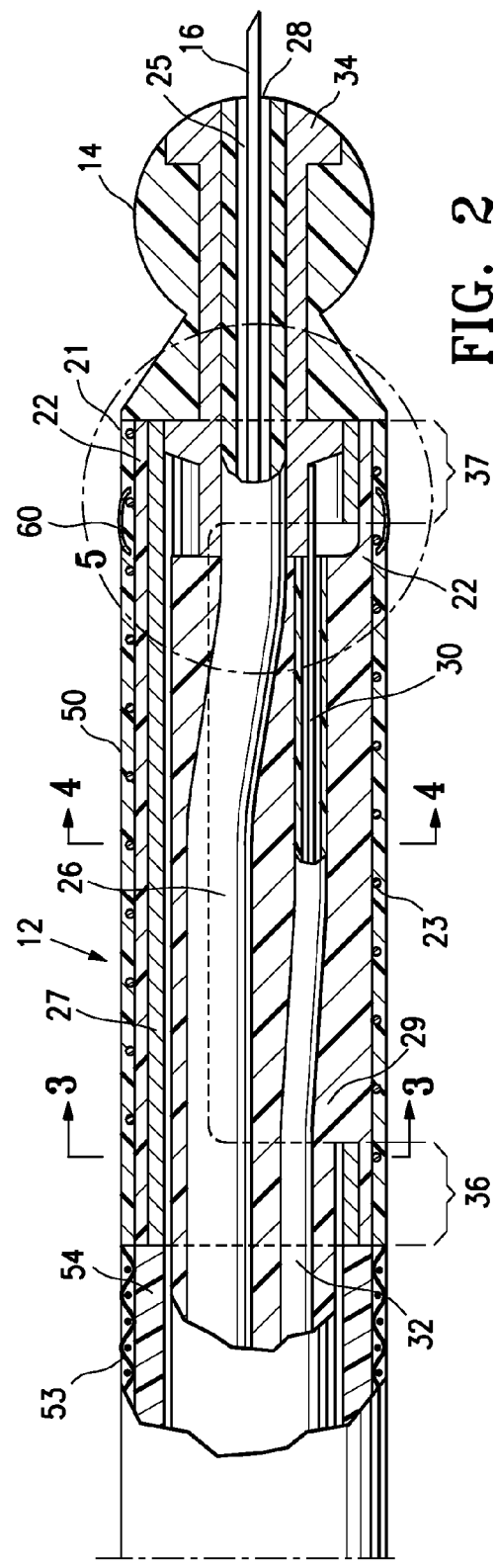
FIG. 1
FIG. 2

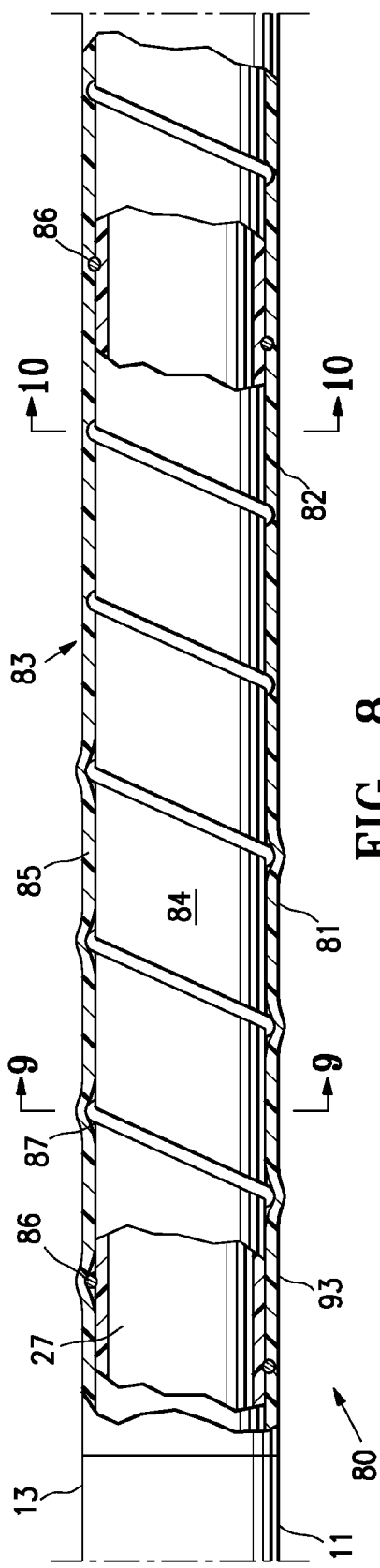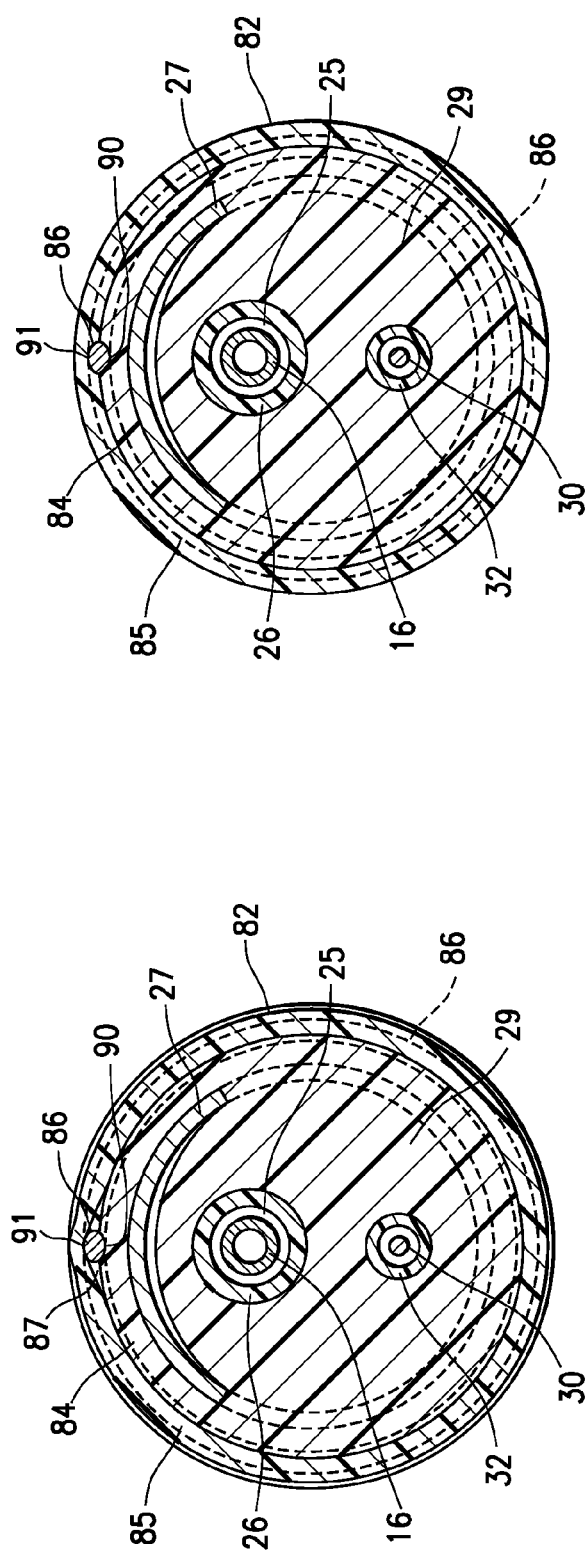
FIG. 8
FIG. 9
FIG. 10

VISUALIZATION OF A CATHETER VIEWED UNDER ULTRASOUND IMAGING

CROSS-REFERENCES TO RELATED APPLICATIONS

This application is a continuation-in-part of prior pending U.S. application Ser. No. 12/044,704, filed Mar. 7, 2008, which is a continuation-in-part of prior pending U.S. application Ser. No. 11/293,420, filed Dec. 2, 2005, both of which are incorporated by reference herein in their entireties.

BACKGROUND OF THE INVENTION

The invention relates to the field of medical devices, and more particularly to catheters, such as needle catheters or other elongated devices configured for inserting into a patient's body lumen or cavity to perform a diagnostic and/or therapeutic procedure.

An essential step in treating or diagnosing cardiac tissue or cardiovascular diseases using an interventional catheter is the proper placement of the catheter at a desired location within the patient, which consequently requires accurate imaging of the catheter location within the patient. Although various methods of imaging catheters within a patient are possible, ultrasonic imaging (also referred to as sonic, acoustic or echo imaging) would provide several advantages. For example, ultrasonic imaging is very safe for the expected extended imaging time periods required for catheter diagnostic and/or therapeutic guidance, unlike imaging methods which expose the patient to x-rays such as CT/EBCT (Electron Beam Computed Tomography) or bi-planar fluoroscopy. Additionally, ultrasound is relatively inexpensive compared to other imaging modalities such as MRI or CT/EBCT, and ultrasound can provide many of the functional diagnostics, such as cardiac wall motion and thickness information, which these expensive modalities provide.

However, one difficulty has been visualization anomalies, including artifacts, lack of an image of catheter sections, and overly bright and/or large images of other catheter sections, in the ultrasonic images of catheters. Such artifacts can provide a misleading and inaccurate impression of the shape and/or location of the catheter within the patient's anatomy. Catheter elements can appear so bright and large on the ultrasonic image (called "blooming") due to their direct highly sonic reflective nature relative to the anatomy, especially at the gain settings typically used to image the anatomy, that the image of the adjacent anatomy is obscured by the catheter image. For example, metallic portions of catheters can produce strong/high amplitude direct echoes (bright images), and a ringing artifact in the form of a pyramid shape of reverberation ("ringing") images on a three-dimensional ultrasonic imaging system, and a triangular shape of reverberation images on a two-dimensional ultrasonic imaging system, trailing off in the viewing direction. Similarly, most thermoplastic catheter shaft surfaces produce strong/high amplitude direct echoes formed by the reflection of sonic energy off a catheter material interface or surface perpendicular to the viewing direction and directly back to the ultrasonic transducer. If the gain settings of the ultrasonic imaging system are reduced to improve the image of the catheter shaft portions by reducing its image and artifact brightness, the image of the anatomy fades to the point of being significantly less visible or not visible at all. Additionally, given that most thermoplastic catheter shafts and their components are smooth (i.e., surfaces/material interfaces that behave as smooth surfaces at the ultrasonic frequencies of interest), the portions of the catheter shaft being imaged at oblique angles reflect the sonic energy away from the ultrasonic transducer and produce a very faint/small image or no image of the catheter shaft surface, which obviously is problematic. For example, locations in the displayed image where the catheter shaft produces no image may be falsely interpreted as the location of the distal end of the catheter and result in the improper or undesired positioning of the catheter. However, if the gain settings of the ultrasonic imaging system are increased to improve the image of these portions of the catheter shaft (increase its image brightness), the image of the anatomy, direct echo catheter surface/material interface images and any artifacts enlarge and brighten significantly, increasing the degree to which they obscure the image of the catheter shaft and the location of adjacent tissue surfaces. Therefore, it would be a significant advance to provide a catheter with improved imaging characteristics by two-dimensional and three-dimensional ultrasonic imaging systems for enhancing the ability to guide and visualize a catheter in the patient's anatomy during diagnostic and/or therapeutic procedures.

SUMMARY OF THE INVENTION

The invention is directed to a catheter for use in a patient's body lumen, having a shaft section configured to minimize ultrasonic image artifacts and the direct ultrasonic image brightness of the shaft surface and its internal components, and to produce its image (i.e., appear) at a wide range of imaging angles, preferably with an intensity not substantially different than surrounding tissue of the patient's body lumen under ultrasound visualization. The shaft section is operative for the desired use of the catheter, yet is also configured to facilitate accurately imaging the shape and location of the shaft section, and easily differentiate it from the surrounding anatomy, without unduly obscuring the images of the adjacent anatomy, using an ultrasound imaging system.

In a presently preferred embodiment, the catheter is an agent delivery catheter having a deflectable distal shaft section with a port configured for delivery of an agent (e.g., a fluid) in a patient's body lumen. The shaft surface and/or its internal components which make the distal shaft section reversibly deflectable and configured for agent delivery typically produce image artifacts and are highly reflective in the body lumen in the sense of producing very bright and large (relative to the brightness of the surrounding tissue) direct reflection echo images of the shaft on an ultrasound imaging system, with artifacts caused by reverberation ("ringing") images trailing off in the viewing direction and/or high amplitude side-lobe reflections that can falsely represent the shaft's location and shape (e.g., degree of deflection). An ultrasound system's probe/transducer typically transmits sonic energy at lower levels that propagate at oblique angles away from the surface of the transducer, called side lobes. If the sonic energy of these side lobes is strongly reflected back to the transducer, an image is formed from the received echo assuming that the echo is a reflection from the sonic energy that moved directly away from the transducer (perpendicular to the surface of the transducer). Thus, an image is formed from the side lobe reflections at a location that is not the actual location of the shaft. Additionally, catheter shafts and their material interfaces often have atraumatic smooth surfaces/interfaces that send obliquely reflected sonic energy in directions away from the ultrasonic transducer and thus, produce no or a very faint/small shaft image. If a catheter shaft contains components that are metallic, the sonic energy that they absorb may essentially bounce around inside the component for a period of time and then a portion of it may exit the component in the direction of the ultrasonic probe/transducer at intervals, producing "ringing" images behind the actual position of the catheter shaft or metallic component (i.e., a greater distance from the ultrasonic transducer). If this "ringing" image was produced at an oblique imaging angle, the only image will appear behind the actual position of the catheter shaft or metallic component. The thermoplastic polymers and polymer mixtures commonly used to form catheter distal shaft sections often produce a direct reflection artifact due to its high reflectivity that is a large bright blob on a 2D ultrasonic imaging system or a large bright blob centered on a long bright curved line, at right angles to the actual shaft, on a 3D ultrasound imaging system display under tissue imaging conditions. However, a catheter of the invention has one or more acoustic impedance selected, echo diffusive and dampening polymeric layer(s) on at least a portion of at least the deflectable distal shaft section, which are preferably configured to render the otherwise highly directly echogenic and/or artifact producing deflectable distal shaft section substantially echolucent. The deflectable distal shaft section is also provided with an echogenic member configured to provide an improved ultrasonic image of at least the deflectable distal shaft section, such that an ultrasonic image of the deflectable distal shaft section preferably consists essentially of the sonic reflections and/or transmissions of the echogenic member in the deflectable distal shaft section (the deflectable distal shaft section being otherwise rendered substantially echolucent by the echo diffusive and dampening layer(s)). In one embodiment the catheter generally has at least one echo diffusive and dampening polymeric layer, which is an outer layer having an acoustic impedance which is between an acoustic impedance of blood and an acoustic impedance of an adjacent layer of the section of the shaft underlying the echo diffusive and dampening polymeric layer, and an echogenic member at least partially embedded in the echo diffusive and dampening polymeric layer. However, in a presently preferred embodiment, the catheter further includes an echo diffusive and dampening inner layer extending along an inner surface of the echo diffusive and dampening outer layer, and the inner and outer echo diffusive and dampening inner and outer layers are configured to have different acoustic impedances, and produce sonic reflections that destructively interfere within a range of ultrasound frequencies of the ultrasound imaging system.

Although discussed primarily in terms of configuring a deflectable distal catheter shaft section for being imaged by an ultrasound imaging system, it should be understood that a intraluminal catheter of the invention more generally has at least a section which is configured for ultrasound imaging in accordance with the invention. The shaft section configured for ultrasonic imaging extends along at least a section of the shaft, typically at least along a distal section of the shaft. The shaft section is formed at least in part of a metallic member, or contains a metallic member like a guidewire, a lumen or other components, materials or features that normally produce strong direct echoes, and/or produce weak echoes from oblique angles, and/or produce ringing artifacts. The echo diffusive and dampening layers thereon render the shaft section (which would otherwise exhibit ringing artifacts and/or be highly directly echogenic relative to the adjacent tissue) substantially echolucent, and the echogenic member located between the two layers provides the desired ultrasonic image of the shaft section.

The echo diffusive and dampening layers are formed of a polymeric material(s), and optionally mixed with particles such as metallic particles having a high density relative to the polymeric material(s), to achieve the desired acoustic impedance, and sonic diffusive and dampening characteristics.

The echogenic member is preferably a rounded or curved member or members extending helically along or circumferentially around the distal shaft section, such as a round metal wire(s) coiled around the shaft section. The echogenic member is preferably located between the two echo diffusive and dampening layers, and is configured at least in part with a curved surface to diffusely reflect a portion of the incident sonic energy back to the transducer of the ultrasonic imaging system at a wide range of incident angles to produce a shaft image with a brightness near that of the adjacent tissues irrespective of the imaging angle (direct or oblique). Although discussed primarily in terms of a coiled metal wire member, other, less easily mounted (and thus less preferred), configurations such as a series of rings or beads with a curved outer surface and mounted circumferentially at intervals along the length of the shaft section can alternatively be used as the echogenic member having a variety of suitable cross sectional shapes. In a presently preferred embodiment, the echogenic member is comprised at least in part of a metal or a blend/alloy containing a metal or metals. It should be understood that the echogenic member is a different member than the metallic member(s) of the distal shaft section having the echo diffusive and dampening layers thereon. A metal bearing echogenic member allows the echogenic member to be thin and thus to not substantially increase the outer diameter of the shaft section. This is preferred at least in part because smaller diameter shafts have fewer insertion site complications. In a presently preferred embodiment, the distal shaft section has a substantially smooth outer surface. In other embodiments, the echogenic member causes a small raised surface at the outer diameter of the shaft.

In one embodiment, the shaft distal section has an electrode, or other sensing or transmitting component (e.g., a transducer, electrical sensor, fiber optic sensor), imbedded or in contact with at least the echo diffusive and dampening outer layer, and one aspect of the invention is directed to configuring the sensing or transmitting component to minimize its echo amplitudes and artifacts while having a brightness that facilitates ultrasonic visualization of its position on the shaft, and to diffusely reflect a portion of the incident sonic energy back to the transducer/probe of the ultrasonic imaging system at a wide range of incident angles to facilitate its ultrasonic visualization at a wide range of imaging angles (sonic energy incident angles). In embodiments in which the sensing/transmitting component (e.g., electrode) is mounted on the deflectable distal shaft section, it should be understood that the section of the shaft that is rendered substantially echolucent by the echo diffusive and dampening layers is the rest of the deflectable distal section not having the sensing/transmitting component mounted thereto. In a presently preferred embodiment, the sensing/transmitting component is connected to the echogenic member. In this embodiment, the echogenic member is a conductor or optical fiber assembly and may extend to the proximal portion of the catheter to function as an electrical and/or fiber optic cable to a catheter connector or be operatively connected to such a cable. Although discussed primarily in terms of providing the electrical connection for an electrode, it should be understood that the echogenic member may act as the cable for a variety of transducers and/or sensors mounted on the shaft in other embodiments.

In one presently preferred embodiment, a catheter of the invention comprises an elongated shaft having a proximal end, a distal end, a tubular member defining an agent delivery lumen extending from the proximal to the distal end of the shaft, and a deflectable distal shaft section having a deflection restoring metal cage which has a distal section of the agent delivery tubular member extending in the metal cage. The deflectable distal shaft section has an echo diffusive and dampening polymeric inner layer on an outer surface of the cage and filling the spaces inside the shaft and cage not occupied by other shaft components or features, and an echo diffusive and dampening polymeric outer layer which is on an outer surface of the inner layer and which preferably has a smooth outer surface. The polymeric materials and the outer layer's thickness are chosen such that the inner and the outer layers have different acoustic impedances that produce direct or close to direct sonic reflections (echoes) at their outer surfaces that propagate to the ultrasonic transducer with substantially equal amplitudes and destructively interfere at the ultrasonic frequencies of interest. The echoes destructively interfere due to the difference in the path lengths to the ultrasonic transducer(s) of the echoes originating from the outer surfaces of the inner and outer layers. The sonic energy reflecting off of the outer surface of the inner layer (echoes) must travel into the shaft through the outer layer thickness and then through the outer layer thickness again to travel out of the shaft, whereas the sonic energy reflecting off of the outer surface of the outer layer doesn't travel this distance. This introduces a phase shift between the sinusoidal sonic energy reflections from the outer surfaces of inner and outer layers arriving at ultrasonic transducer(s) such that they destructively interfere with each other (lowers the amplitude of the detected sonic energy at the transducer(s)) at frequencies determined by the thickness of the outer layer and the velocity of sound in the outer layer.

An echogenic curved surface metal wire member is helically extending longitudinally along and between the inner and outer layers, such that an ultrasonic image of the deflectable distal shaft section consists essentially of the sonic reflections or transmissions originating from the metal wire member in the deflectable distal shaft section which is otherwise rendered substantially echolucent by the echo diffusive and dampening inner and outer layers and its smooth outer surface.

The deflectable distal shaft section having the coiled metal wire member or other echogenic member(s) between the two echo diffusive and dampening layers is preferably configured to produce a shaft image that is substantially the same brightness as the images simultaneously produced of the surrounding tissue of the patient's body lumen, and that is at or nearly at the shaft's actual location in the anatomy, and with echo amplitudes and timing that produce a shaft image size/width that is substantially equal to the shaft's actual size with the gain of the ultrasonic imaging system set to optimally image the patient's heart or other adjacent anatomy. For use with two-dimensional (2D) ultrasonic imaging systems, the deflectable distal shaft section is preferably configured to produce a shaft image that is a continuous (i.e., an elongated tubular shape) shaft image. In contrast, for three-dimensional (3D) imaging applications, it is preferred that it produces a discontinuous shaft image (e.g., a series of short diagonal lines, a dashed line and/or a dotted line), at least along a portion of the deflectable distal shaft section. In two-dimensional imaging applications, a discontinuous image can result in displayed images that lack a discernable image of the shaft and therefore, a discontinuous image is not preferred. However, in three-dimensional imaging applications, a discontinuous shaft image is displayed in the imaging volume as a series of short diagonal lines, a dashed line and/or a dotted line in the most useful three-dimensional image display formats (for example, see-through formats and surface formats).

In three-dimensional image display formats, a discontinuous shaft image is so different from the anatomy image that the shaft image is very easily differentiated from the adjacent anatomy and therefore, a discontinuous shaft image for at least a portion of the shaft is preferred. Additionally, the discontinuous shaft image has a number of advantages including allowing the physician to count the number of discontinuous segments of the echogenic member which are currently visible on the image monitor in order to gauge sizes or distances in the patient's anatomy, or in order to determine whether the key part of the catheter is included in the image. For example, if the discontinuous image portion of the catheter is located at or near to its distal tip or work element, then counting the number of visible discontinuous segments of the echogenic member in comparison to the known total number will assure that the distal tip or work element is in the image. Variations in the discontinuous shaft image segments can also be exploited to help differentiate different regions of the shaft.

3D embodiments producing only a continuous shaft image (hereafter "the continuous image catheter") are not presently preferred due at least in part to the difficulty of spotting the position of the shaft in the live anatomy. This is because both 2D or 3D echo images of the anatomy also tend to be continuous images. For example, when the continuous image catheter is against a ventricular, venous or arterial wall, its image merges with that of the wall, making the wall appear slightly deformed and/or slightly brighter, which is difficult to find and see in both 2D and 3D echo viewing formats. It is similarly difficult to differentiate a continuous image catheter from papillary muscle or chordae tendineae images in both 2D and 3D echo viewing formats when the continuous image catheter is in the ventricular space. Such difficulties may necessitate deliberately moving the continuous image catheter in order to facilitate detecting its position in 2D or 3D echo viewing formats, although this is obviously not ideal, and is often a highly problematic way to attempt to detect the shaft.

One aspect of the invention is directed to a method of making a catheter having a shaft section which appears with an improved image under ultrasonic imaging in a patient's body lumen, the method generally comprising rendering an otherwise highly directly reflective shaft section (relative to the reflectivity of the tissue being imaged) substantially echolucent by providing an echo diffusive and dampening polymeric inner and outer layer at the shaft section, with none, or one, or both of the inner layer and the outer layer having particles loaded in the polymeric material of the layer, and the outer layer having an acoustic impedance different from surrounding blood in the patient's body lumen and the inner layer having an acoustic impedance different from the outer layer such that the outer surfaces of inner and outer layers produce sonic reflections that propagate back to the transducer of substantially equal amplitudes that destructively interfere at the ultrasonic frequencies of interest at or near direct reflection angles, and providing an echogenic member on or within the outer layer and/or inner layer, such that an ultrasonic image of the shaft section consists essentially of echoes originating from the echogenic member of the shaft section which is otherwise substantially echolucent.

In one embodiment, the catheter generally comprises an elongated shaft having a proximal end, a distal end, and a distal shaft section formed at least in part of a metallic member, and the distal shaft section has an echo diffusive and dampening polymeric inner layer on an outer surface of the distal shaft section, and an echo diffusive and dampening polymeric outer layer on an outer surface of the inner layer, and an echogenic member which has an outer surface and which is between the inner and outer layers, and the distal shaft section has a first longitudinal portion configured to produce a discontinuous shaft image and along which the echogenic member is fully encapsulated by the inner and outer layers, and a second longitudinal portion configured to produce a continuous shaft image and along which the echogenic member outer surface is in part separated from adjacent surrounding surfaces of the inner and outer layers by a gap such that the echogenic member is not fully encapsulated. Typically, the inner and outer layers along the second portion (i.e., continuous image producing portion) are in contact with each other around a substantial fraction of the circumference of the inner layer but are not fused together or otherwise in intimate contact with each other therearound, whereas the inner and outer layers are typically fused together along the first (discontinuous image) portion. In a presently preferred embodiment, the continuous image portion is a proximal portion of the deflectable distal shaft section, and the discontinuous image portion is a distal portion of the deflectable distal shaft section.

A catheter of the invention results in an image of at least a portion of the catheter on an ultrasound imaging system's display that is substantially free of the usual shaft image artifacts that falsely represent the shaft's location and that obscure adjacent tissue images with large and very bright images. The catheter has at least a shaft section that produces a shaft image with a brightness/intensity similar to that of the tissue of the surrounding anatomy, and with a size (diameter) substantially similar to the shaft's actual size. Additionally, the catheter shaft produces this image from a wide range of imaging angles. The produced shaft section image may be a continuous image, a discontinuous image, or contain one or more continuous and discontinuous image sections, as preferred for the image display format and the portions of interest of the shaft. Moreover, in addition to improving the visualization of the catheter under ultrasonic imaging, the catheter shaft is configured to facilitate the atraumatic advancing, maneuvering, and positioning the operative distal end at a desired location in the patient's body lumen to perform a medical procedure. These and other advantages of the invention will become more apparent from the following Detailed Description and accompanying exemplary drawings.

BRIEF DESCRIPTION OF THE DRAWINGS

FIG. 1 is an elevational view, partially in section, of an agent delivery needle catheter embodying features of the invention.

FIG. 2 is an enlarged, longitudinal cross sectional view of the catheter of claim 1, taken along line 2-2.

FIG. 8 is an elevational view of an agent delivery needle catheter distal section embodying features of the invention, having a distal portion along which the echogenic member is fully encapsulated by the inner and outer layers, and a proximal portion along which the echogenic member outer surface is in part separated from adjacent surrounding surfaces of the inner and outer layers by a gap such that the echogenic member is not fully encapsulated.

FIGS. 9 and 10 are a transverse cross sections of the catheter of FIG. 8, taken along lines 9-9 and 10-10, respectively.

DETAILED DESCRIPTION OF THE PREFERRED EMBODIMENTS

Figure 3:
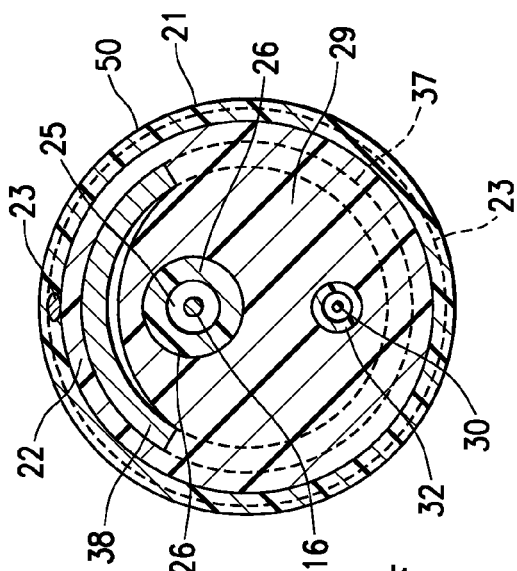
FIGS. 3 and 4 are a transverse cross sections of the catheter of FIG. 2, taken along lines 3-3 and 4-4, respectively.

FIG. 1 illustrates a catheter 10 which embodies features of the invention, configured for being viewed under ultrasonic imaging using an ultrasound imaging system (not shown). In the embodiment illustrated in FIG. 1, the catheter 10 is an agent delivery needle catheter generally comprising an elongated shaft 11 having a proximal end, a distal end, a deflectable distal shaft section 12, and a proximal shaft section 13. The shaft 11 has a distal tip member 14, and a needle 16 slidably disposed in a lumen of the shaft 11 has an extended configuration in which the needle distal end extends distally from the distal end of the shaft tip and a retracted configuration (not shown) in which the needle distal end is proximally retracted into the catheter lumen (e.g., retracted into the distal tip member 14). A proximal adapter 19 on the proximal end of the shaft controls the shaft deflection, needle extension length and needle position, and provides operative connectors such as the connector having port 20 configured for providing access to the needle 16 for delivery of an agent, or for aspiration, through the lumen of the needle 16. A variety of operative connectors may be provided at the proximal adapter depending on the desired use of the catheter 10. To deliver an agent to a desired treatment location, the catheter is advanced through the patient's tortuous vasculature to the desired treatment location in a body lumen of the patient, the needle 16 is extended from the distal tip member 14 and into a wall of the body lumen at the treatment location, and an agent is infused from the needle 16 into the body lumen wall, and the needle 16 is then retracted back into the catheter 10 and the catheter repositioned or removed from the patient's body lumen.

FIG. 1 illustrates a partially in section view of the catheter 10, and specifically with an outer layer 21 of the deflectable distal shaft section 12 partially broken away to show an inner layer 22 beneath the outer layer 21, and an echogenic metal wire member 23 extending helically between the inner and outer layers 21 and 22. The inner and outer layers 21, 22 are echo diffusive and dampening polymeric layers. In a preferred embodiment, one of the inner layer 22 and the outer layer 21 has particles loaded in the polymeric material of the layer, and the layers 21, 22 are configured such that the inner and the outer layers have different acoustic impedances, and produce sonic reflections in the patient's body of substantially equal amplitudes that destructively interfere at substantially direct imaging angles at frequencies of interest, such that an ultrasonic image of the deflectable distal shaft section 12 consists essentially of sonic reflections of the echogenic wire member 23 in the deflectable distal shaft section which is otherwise rendered substantially echolucent (producing a very faint or no image on an ultrasound imaging system) by the echo diffusive and dampening inner and outer layers, as discussed in more detail below.

Figure 4:
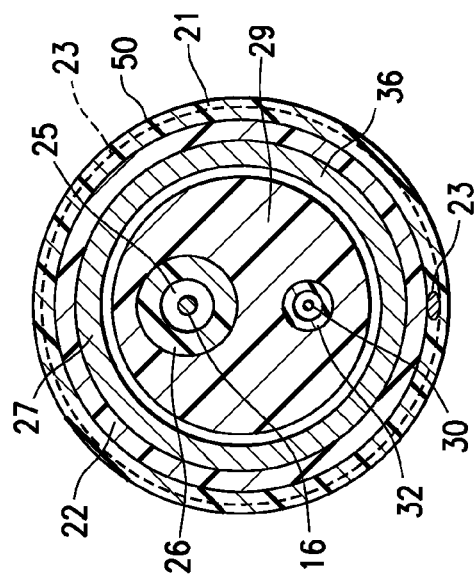

FIG. 2 illustrates an enlarged longitudinal cross sectional view of the catheter of FIG. 1, taken along line 2-2, and FIGS. 3 and 4 are a transverse cross sections of the catheter of FIG. 2, taken along lines 3-3 and 4-4, respectively. In the illustrated embodiment, the shaft 11 comprises a tubular body member 50 of multiple members and sections joined together, with a relatively flexible section along the deflectable distal shaft section 12 and a relatively less flexible section along the proximal shaft section 13. More specifically, the catheter shaft 11 has a tubular member 26 defining an agent delivery lumen 25 extending from the proximal to the distal end of the shaft 11, with the agent delivery needle 16 slidably disposed in the lumen 25. The deflectable distal shaft section 12 has a deflection restoring metal cage 27 which has a distal section of the agent delivery needle 16 and tubular member 26 extending therein. The metal cage 27 in the distal shaft section 12 in the illustrated embodiment is formed of a metallic tube with a slot or other large opening along a section of the cage forming an open arc section, such that the cage is configured to deflect laterally, for example as described in U.S. patent application Ser. No. 10/676,616, incorporated by reference herein in its entirety. In the illustrated embodiment the arc section 38 (illustrated in dashed line in part behind the tubular member 26 in FIG. 2) extends around about 90 degrees as best shown in FIG. 4 illustrating a transverse cross section of FIG. 2, taken along line 4-4. The cage 27 has tubular proximal and distal ends 36, 37 at either end of the arc section 38, where the cage wall extends continuously around the 360 degree circumference (see dashed lines in FIG. 4 illustrating the tubular distal end 37 of the cage). However, the cage can be formed of a variety of suitable structures including wires, a thin metallic strip(s), a tube(s), or a combined construction that provides a restoring force to the deflectable distal section 12 of the shaft.

Catheter 10 has a deflection member 30 (e.g., a tendon wire) connected to a deflection control mechanism 31 at the proximal adapter 19, for deflecting the distal end of the catheter 10. To effectively deflect the distal end of the catheter the deflection member 30 is preferably near the surface of the shaft in the deflecting (curving) portion as far away as practical from section 38. However, a catheter having the echo diffusive and dampening layers 21, 22 and echogenic member 23 in accordance with the invention can have a variety of suitable catheter configurations including a non-deflecting configuration. The deflection member 30 extends within a lumen of a second inner tubular member 32, and is secured to the shaft adjacent to the distal end of the tubular body member 50. In the illustrated embodiment, a stabilizing tubular member 29, typically comprising a dual lumen extrusion, is positioned within at least a section of the cage 27 to stabilize the position of the inner tubular members 26, 32 therein. The stabilizing member 29 is formed of a single section or multiple longitudinally adjacent sections of the tubing, and has a proximal end typically located within the cage 27 or a short distance proximal thereto. In one presently preferred embodiment, the stabilizing member 29, or other tubular portion of the shaft 11 extending along the inner surface of the metal cage 27, is formed of the same polymeric material as the inner layer 22. Along the arc section 38 of the cage, part of the inner layer 22 is separated from the stabilizing member 29 by the cage, whereas the remaining part of the inner layer (around the circumference thereof) is fused to the stabilizing member 29. Although, for ease of illustration, a slight gap between the inner surface of the cage 27 and the outer surface of the stabilizing member 29 is shown in FIG. 2 and in the corresponding sectional views of FIGS. 3, 4 and 5, it should be understood that the inner surface of the cage contacts the underlying sections of the stabilizing member 29. In the embodiment illustrated in FIG. 2, the catheter distal end functions as an electrode and is electrically connected to an electrical connector 41 which is provided at the proximal adapter 10 for connecting the catheter 10 to diagnostic or therapeutic equipment (not shown). Specifically, in the illustrated embodiment, a metal pin 34 in the distal tip 14 is electrically connected to the tendon wire 30, which acts as a conductor wire electrically connecting the pin 34 to connector 41. Additionally, a band electrode 60 is mounted on the deflectable distal section 12, as discussed in more detail below.

The outer and inner layers 21, 22 have composition and dimensional (thickness) characteristics designed to render the deflectable distal shaft section 12 substantially echolucent apart from the sonic reflections of the coil member 23. The substantially echolucent distal section should be understood to refer to the length of the shaft not having a metal band such as band electrode 60 mounted thereon. The substantially echolucent portion of the shaft produces direct echo amplitudes received by the imaging system probe/transducer substantially near to or preferably lower than those produced by the adjacent anatomy and thus eliminates artifacts that obscure the image of the adjacent anatomy and/or falsely represent the shaft's location and shape. As a result, sonic energy directed at the catheter inside the body lumen from an ultrasound imaging system outside of the body lumen and reflected off or transmitted from the coil member 23 and received at the imaging system transducer is the bulk of the reflected sonic energy detected by the transducer, to thereby produce an image of the catheter which consists primarily of the sonic reflections or transmissions of the coil member 23. Thus, ultrasonic image artifacts and overly bright images caused by echoes originating from the surface and the internal portions of the deflectable distal shaft section 12, especially the metallic inner portions such as cage 27 and needle 16, are prevented or minimized due to the two layers 21, 22.

The outer and inner layers 21, 22 are designed to produce echoes in the patient's body of approximately equal amplitude, and which destructively interfere at the substantially direct imaging angles that send echoes toward the ultrasonic transducer. The outer surfaces of outer and inner layers 21, 22 are designed to be smooth at the ultrasonic frequencies of interest, and thus, at substantially oblique imaging angles, reflect echoes that travel away from the ultrasonic transducer. This results in the sonic reflections of the outer interfaces of the layers 21, 22 (i.e., at the interface between the blood and the outer surface of the outer layer 21, and the interface between the outer surface of the inner layer 22 and the outer layer 21) contributing little or nothing to the image of the catheter displayed by the ultrasound imaging system. Moreover, the layers 21, 22 and stabilizing member 29 diffuse/dampen any sonic energy propagating through them and reflecting or transmitting back through the layers from the inner portions of the shaft (i.e., the portions of the shaft inside the inner layer 22 and stabilizing member 29). Thus, the inner and outer layers 22, 21 together minimize the shaft's directly reflected (back to the transducer) echo amplitude, which controls and minimizes the image bloom artifact and side lobe curved image artifact on a 3D imaging system display.

The polymeric materials, preferably elastomeric materials, of the layers 21, 22 move in response to the sonic energy's propagation, which causes a rubbing action between the polymeric molecules and between the polymeric molecules and the particles compounded into the polymer, if any, that converts some of the sonic energy into heat, reducing the amplitude of the sonic energy. This is the basis of the dampening property of the layers 21, 22. A portion of the sonic energy reflects off the particles compounded into the polymer, which increases the path length and residence time of the sonic energy in the filled layer and redirects the sonic energy in random directions. The longer the path length of the sonic energy in the layers 21, 22 (and stabilizing member 29), the more the dampening of the sonic energy. The redirection of the sonic energy in random directions is the basis of the diffusive property of the layer(s). Additionally, it is preferred to choose internal shaft components to have curved surfaces, like the tubular shapes of tubular member 26 and second inner tubular member 32, that produce diffusive reflections to further aid in diffusing any sonic energy that penetrates through the interface of the outer and inner layers 21, 22. The echo reflectivity of the two layers 21, 22 is controlled by adjusting the acoustic impedance of the outer layer relative to that of the blood in the body lumen, and of the inner layer relative to the outer layer. "Acoustic impedance" is a material property well known in the art and defined as the velocity of sound in that material multiplied by the density of the material. In a presently preferred embodiment, the outer layer 21 has an acoustic impedance between that of the blood and the inner layer 22 or other adjacent inner layer of the section of the shaft in the absence of inner layer 22. Specifically, the outer layer 21 has an acoustic impedance near that of blood or the fluid in the body lumen such that it produces direct sonic reflections of substantially equal or lesser amplitudes as the adjacent anatomy, and the echogenic member in or in contact with the first echo dampening polymer is configured to produce echoes of substantially equal amplitudes as the adjacent anatomy at direct and oblique imaging angles, such that an ultrasonic image of the distal shaft section consists essentially of the sonic reflections or transmissions of the echogenic member 23 in the distal shaft section which is otherwise rendered substantially echolucent by the echo dampening polymer.

The polymeric materials are blended to create layer materials with a desired acoustic impedance and velocity of sound if a single polymeric material doesn't provide the desired values. Additionally, a polymeric material or a polymeric material blend may be mixed with particles, such as high density (relative to polymers) metallic particles, to further adjust a polymeric material or material blend to achieve a desired acoustic impedance and velocity of sound, and to achieve other desired characteristics such as radiopacity. The velocity of sound in the outer layer material determines the outer layer thickness required at an ultrasonic frequency of interest to produce destructive interference. The relative acoustic impedances of the blood, outer layer and inner layer (and the sonic energy dissipative characteristics of the outer layer) determine the relative amplitudes of the reflected sonic energy at each material interface according to a well known relationship/equation. The optimum destructive interference occurs when the thickness of the outer layer is equal to or near to a quarter wavelength at an ultrasonic frequency of interest at the velocity of sound in the outer layer and the sonic energies reflected at the blood/outer layer interface and reflected at the outer layer/inner layer interface (and passes through the outer layer and into the blood) are substantially equal. The ultrasonic frequencies of interest are frequencies at or near the center frequency of the imaging system's ultrasonic probe/transducer, frequencies within the probe's ultrasonic bandwidth (generally the range of frequencies between the half power frequency components), and/or echo ultrasonic frequencies used by the ultrasonic imaging system to create images. In some echo system modes and in anticipated echo systems, received echo frequencies that are harmonic of the primary frequency range or represent a high end of the primary frequency range are preferentially used to create the image.

In constructing the catheter 10, the thickness of the layers 21, 22 is constrained by certain practical considerations. Specifically, if the composition of the outer layer is such that the speed of sound therein is relatively high, then the outer layer will have to be made relatively thick to be at or near a quarter wavelength thickness, which may increase the shaft outer diameter by an amount disadvantageous to catheter performance. In contrast, if the speed of sound in the outer layer is very low, the outer layer would have to be made too thin to control adequately without expensive and/or time consuming manufacturing processes. In general, an outer layer thickness in the range of 0.002 inches to about 0.010 inches may be applied and adequately controlled using conventional catheter shaft construction methods and processes without unreasonably increasing the shaft outer diameter.

Thus, the outer layer 21 is applied at or near a quarter wavelength thickness to cause approximately a one half wavelength shift between the two echo waveforms reflected from the outer surfaces of the two layers 21, 22, to cause the destructive interference of the two echoes, especially when the sonic energy is directed at the shaft surface at a 90 degree angle or close to a 90 degree angle (direct image angle/direct echoes). More specifically, in a presently preferred embodiment, the thickness of the outer layer 21 is a quarter of the wavelength of the center frequency of the ultrasound waves emitted by the ultrasound imaging device.

The layer acoustic impedance is adjusted by selecting the polymeric material (i.e., a single polymer or a mixture of polymeric materials) and amount of an optional particulate compounded with the polymer. In a presently preferred embodiment, the outer layer 21 has tungsten particle filings/powder compounded with the polymeric material of the outer layer, although the tungsten particles could additionally or alternatively be provided in the inner layer 22. The particles have a size and composition configured to help dissipate and diffuse sonic energy. The greater the total surface area of the particles that interface with the polymer, the more dissipative the blend, thus favoring smaller particles (it should be noted that the smaller the particles, the higher the frequency must be for sonic energy to be effectively reflected by the particles). Additionally, the greater the difference in acoustic impedance between the composition of the polymer and the particles, the more the sonic energy will be randomly reflected by the particles in the compound, increasing sonic energy dissipation and diffusion. Alternative particulates for compounding in the outer layer 21 (or inner layer 22) include glass, calcium, calcium carbonate, acetals, silicones and many other materials or compounds of suitable acoustic properties. In more complex embodiments, gas filled voids can function sonically as particulates, and particles of different size and composition may be used to attain the desired sonic dissipative and diffusive properties. The tungsten or other dense particles render the shaft sufficiently radiopaque to facilitate viewing the distal shaft section 12 fluoroscopically in the body lumen. The percent loading of the radiopaque particles in the outer layer 21 or inner layer 22 can range from about 0% to about 90% by weight of the blend.

The outer surface of the outer layer 21 and inner layer 22 is preferably substantially smooth (i.e., smooth within normal manufacturing tolerances, and not intentionally roughened or irregular). The outer layer may be applied to the inner layer by friction fitting, as for example in an embodiment in which the layer 21 is formed of an elastomeric material such as polyurethane which is applied by allowing a temporarily expanded layer 21 to retract down onto the inner layer 22. Alternatively or in addition, the outer layer may be formed over the inner layer 22 using a heat shrink fusion type of method. Generally, in the heat shrink fusion method, a tube of the outer layer material is place over the inner layer 22, a heat shrinkable tube is placed over the tube of the outer layer material, heat is applied to the heat shrinkable tube to melt the outer layer material as the heat shrinkable tube shrinks to form the outer layer 21 over the inner layer 22 and then the heat shrinkable tube is removed. Other well known polymer jacket application methods may also be used. Sonic energy that is not incident to the shaft at or near 90 degrees (an oblique imaging angle) is reflected away from the ultrasonic transducer by the smooth outer surface, and thus produces no image. The smooth surface is thus configured to minimize the contribution to the ultrasonic image of the deflectable distal shaft section caused by sonic reflections reflected off the substantially smooth outer surfaces, by maximizing the percentage of the sonic reflections which are directed away from the transducer. A smooth outer layer 21 outer surface is also less traumatic when advanced or retracted in vessel than a roughened or irregular outer surface.

Because the outer and inner layers 21, 22 and stabilizing tubular member 29 render the deflectable distal shaft section substantially echolucent, the echogenic member 23 is provided on the distal shaft section 12 to provide an ultrasonic image of the deflectable distal section of the shaft. In the illustrated embodiment, the echogenic member is the metallic round metal wire member 23 that is helically extending longitudinally along and between the inner and outer layers 22, 21. The wire 23 is typically a small outer diameter (e.g., 0.004 inch) insulated electrical conductor wire embedded between the two layers 21, 22, and in a presently preferred embodiment does not protrude along the outer surface of the deflectable distal shaft section 12 for improved low profile and shaft advanceability. The curved outer surface of the wire 23 on the portion of the shaft facing the transducer reflects a portion of the incident sonic energy back to the transducer from a wide range of sonic energy incident angles, so that the wire renders the echoes produced by the distal shaft section 12 relatively insensitive to the incident angle of the sonic energy from the transducer to the surface of the shaft. Additionally, the layers 21, 22 in contact with the wire 23 dampen the sonic energy that enters, travels in and may then exit the wire 23, so that the ringing images that would otherwise be produced by the wire 23 are minimized. More than one wire 23 may be incorporated into the shaft in alternative embodiments. The echogenic member 23 preferably has a length substantially equal to the length of the cage 27 and outer and inner layers 21, 22.

Although in the illustrated embodiment, the helical wire 23 is at the interface of the outer and inner layers 21, 22, the echogenic member can be incorporated into a shaft at other positions relative to the layers. For instance, if the outer layer 21 is much thicker than the desired thickness of the echogenic member, the echogenic member may best reside entirely within the outer layer or even have a portion exposed on the outer diameter of the shaft, at least at some longitudinal positions along the shaft. An exposed portion of helical wire 23 may act as an ECG sensing electrode. In other instances, if the outer layer is thin and/or thin compared with the desired thickness of the echogenic member, the echogenic member may best reside entirely within the inner layer 22. Thus, although the echogenic helical member 23 has an outer diameter (i.e., the diameter of the tubular structure formed by helically winding the wire 23 around inner layer 22) less than the outer diameter of the outer layer 21 in the illustrated embodiment, in alternative embodiments, the echogenic member can have a larger outer diameter which forms a helical protrusion at the outer surface of the outer layer 21, or a smaller outer diameter.

The catheter may be configured to produce a continuous or a discontinuous shaft image. If a continuous shaft image is desired, the wire member 23 is applied with spaced apart coil turns having a spacing configured such that echoes from individual adjacent turns merge and form a continuous shaft image. Specifically, the residual amount of ringing from the wire and the diffusion of the wire echoes by the outer layer 21 cause the echoes from individual spaced apart adjacent turns of the coiled wire 23 to merge and form a continuous shaft image at the shaft's actual location in the anatomy and with echo amplitudes and residence times of the sonic energy that produce a shaft image size that is substantially equal to the shaft's actual size. Additionally or alternatively, the particle loading of the outer layer 21 may be adjusted to increase the diffusion of the wire echoes and cause the merging of the echoes of adjacent turns of wire 23. The coiled wire 23 is typically applied onto the inner layer before the outer layer is applied thereon. A coiled wire 23 pre-embedded in the outer layer 21 or the inner layer 22 could alternatively be used. Because the coil extends coaxially around and near the outer circumference of the shaft 11, unlike a coil placed inside a lumen of the catheter, its ultrasound image can be closely matched to the size and shape of the catheter shaft 11, and the coil 23 preferably does not increase the shaft profile or use shaft wall space in such a way or to such an extent as to materially decrease the shaft strength.

If a discontinuous shaft image is desired, the wire member 23 is applied with an increased pitch configured such that echoes from individual adjacent turns do not merge. The residual amount of ringing from the wire and the diffusion of the wire echoes by the outer layer 21 cause the echoes from individual spaced apart adjacent turns of the coiled wire 23 to form individual images at the shaft's actual location in the anatomy and with echo amplitudes and residence times of the sonic energy that produce a discontinuous shaft image size that is substantially equal to the shaft's actual size, but represented as a series of diagonal lines, dashes and/or dots. Additionally or alternatively, the particle loading of the outer layer 21 may be adjusted to decrease the diffusion of the wire echoes and cause the unmerging of the echoes of adjacent turns of wire 23.

The spacing between adjacent turns of the coil relative to the diameter of the coil and shaft is not necessarily to scale in FIG. 2, for ease of illustration. The larger the number of coil turns per unit length the brighter and the more likely to be continuous is the ultrasonic image produced thereby. In one embodiment, the coil pitch is at least about 4 mm for a discontinuous shaft image, and not more than about 3 mm for a continuous shaft image in an otherwise identical shaft section. The echogenic member 23 structure is easily manipulated to obtain the desired shaft image based on imaging test results. In addition to the coil turn spacing, a number of factors effect the image produced by the helical member 23, such as the wire wall thickness, helical diameter, and nature of the material in contact with the echogenic member 23. For example, all other parameters being equal, the larger the thickness or greater the mass of the echogenic member, the brighter and larger (outer diameter (OD)) the shaft image, the greater its tendency to produce ringing artifacts and the greater the distance between adjacent echogenic members or echogenic member wraps may be and still produce a continuous shaft image; the greater the coil diameter, the larger the shaft (OD) image will be; the greater the sonic energy dissipative (dampening) properties of the layer materials in direct contact with the echogenic member or the greater the contact area of the echogenic member with the dissipative material, the closer together adjacent echogenic members or echogenic member wraps must be to produce a continuous shaft image and the smaller (OD) the shaft image will appear; the lower the modulus of a polymer or polymer mixture, the more the sonic energy dissipative (dampening) it will be; the more diffusive the (layer) materials in direct contact with the echogenic member or the greater the contact area of the echogenic material with the diffusive material, the further apart adjacent echogenic members or echogenic member wraps may be and still produce a continuous shaft image and the larger (OD) the shaft image will appear.

For example, if continuous and discontinuous shaft image portions are desired, it may be obtained in designs where the discontinuous image portion is constructed with the wire 23 wrapped with a larger pitch than in the continuous image portion. In another example, it may be obtained by designing the outer jacket 21 applied over the desired discontinuous imaging shaft portion to be less diffusive and/or more damping than the outer jacket 21 applied to the desired continuous imaging shaft portion. In another example, it may be obtained by designing discontinuous imaging shaft portion to have a smaller OD wire 23 which is positioned nearer the outer surface of the layers 21, 22 than wire 23 of the continuous imaging shaft portion. Naturally, in more complex embodiments, multiple design parameters may be adjusted to produce suitable continuous and/or discontinuous imaging shaft portions.

The nature of the discontinuous image can be exploited to facilitate guidance and positioning of catheter. This is not only because a discontinuous image is so different from the anatomy image that the catheter image is very easily differentiated from the adjacent anatomy. By designing the catheter to have a specific known number of diagonal lines, dashes or dots in the catheter's discontinuous image, if the physician is not able to view all of the diagonal lines, dashes or dots (for instance, counting from a proximal shaft portion that produces a continuous shaft image or other image landmark), then it is clear that the current 3D view of the anatomy doesn't include a view of that portion of the catheter. The physician can then adjust the view/image/imaging probe (transducer) to include/image/view the catheter portions of interest, follow and "connect the dots" to estimate where the tip would be if it was visible in the image even when the discontinuous catheter image portion is curved or deflected. In contrast, with a continuous shaft image, any break in the image of the catheter (e.g., merging of the catheter image with an anatomy wall or other structure's image) can be easily mistaken for the distal end of the catheter echogenic member and result in a positioning or location error. In another instance, a catheter may have more than one portion of interest (for example, device attachment sites or catheter portions that must be positioned a different anatomy sites to deploy or function) and each device portion of interest could be differentiated in the image by differences in the spacing, shape, size and/or brightness of its adjacent or spanning discontinuous imaging portions. Additionally, for instance, if the discontinuous imaging portion has equally spaced diagonal lines, dashes or dots, then their foreshortening in an image adds to the intuitive 3D nature of an image confined to be displayed on a conventional monitor screen. Such equal spacing also may provide a convenient scale on the display to measure or help perceive the size of the anatomy or distances between image locations of interest.

In an alternative embodiment of the invention, the catheter deflectable distal shaft section has at least one portion along which the echogenic member is not fully encapsulated by the layers, and the echo diffusive and dampening layers are preferably not in intimate contact with each other, such that the resulting shaft image of the portion is continuous. Preferably, the distal shaft section is configured such that a discontinuous image is produced by an adjacent portion of the distal shaft section along which the echogenic member is fully encapsulated and the echo diffusive and dampening layers are preferably in intimate contact with each other. FIGS. 8-10, discussed in more detail below, illustrate one such embodiment, in which the produced shaft image contains a continuous image section and a discontinuous image section.

In a presently preferred embodiment, the echogenic member 23 is composed, at least in part, of a metal(s) or metal alloy(s). A metallic or metal containing wire component is preferred, because the portion of the incident sonic energy that is coupled into the metallic wire component will rapidly travel in the metal(s) and send sonic energy back into the outer diffusive and dampening layer and thus, back to the ultrasonic transducer to produce a shaft image along a length of the wire component 23. In this embodiment, the dampening properties of the layer(s) in contact with the echogenic member 23 rapidly dissipate the sonic energy that is coupled into the metallic wire component to prevent ringing artifacts of any significance from originating from the echogenic member.

Although preferably formed of copper or a copper alloy, alternative materials for the coil 23 include nickel titanium alloy (NiTi), stainless steel, aluminum or other conductive metal or alloy. In some embodiments, the conductive wire is encased in an insulating jacket or coating. In embodiments in which the echogenic member is not used as an electrical conductive lead wire, the echogenic member may be formed of polymers with sufficiently high acoustic impedances (relative to the layer in contact with its outer surface) and/or shaped to be sufficiently reflective along its length, or a fiber optic cable/glass material, or even a void in the material which is preferably filled with air or gas. Additionally, although illustrated as a unitary coiled wire, a series of members providing a pattern similar to the coiled wire can alternatively be used, such as a coil composed of more than one wire, a series of rings, C-shaped bands, knobs, disks, studs, and the like imbedded in a layer or layers of the catheter. The coiled member 23 is configured to avoid producing the overly bright and ringing images typically produced by a braided, single or multiple coiled layers commonly used as reinforcing members in catheter shaft construction. Specifically, in a preferred embodiment, the coiled member 23 is a single, noncrossing/overlapping strand with relatively large spacing between coil turns (relative to the outer diameter of the wire), and is provided along only a relatively short distal end section of the catheter (e.g., deflectable distal section 12) over metal cage 27 which itself reinforces the shaft therealong. The coiled member 23 thus is not configured to substantially increase the strength of the shaft, unlike typical braided or coiled shaft sections. In fact, providing that the resulting catheter dimensions are acceptable, it is possible to decouple the coiled member 23 entirely from the shaft structure, with it clearly not contributing any appreciable support or stiffness to the shaft structure, yet still functioning as an echogenic member in a catheter of the invention.

The echo diffusive and dampening layers 21, 22 and echogenic member 23 in the illustrated embodiment extend only along the metal cage member 27 of the deflectable distal shaft section 12. However, in alternative embodiments, the layers 21, 22 and echogenic member 23 may be extended proximally onto the proximal section 13, particularly to improve the visualization of embodiments in which the metal cage member 27 is very short. In general, the echo diffusive and dampening layers 21, 22 and echogenic member 23 will extend at least along a shaft section that can be expected to be imaged in the anatomy at a location where an improved shaft image is desired and/or it is desired that the images of the adjacent anatomy not be obscured.

In the embodiment of FIG. 2, ring electrode 60 is mounted adjacent to the distal ends of the layers 21, 22 and echogenic member 23. The electrode 60 is typically provided for pacing, ECG detection, or mapping, and is preferably a band extending continuously around the circumference of the shaft for securely mounting on the shaft. Conventional catheter shaft electrodes are generally thin walled metallic tubes which have a longitudinally flat surface, which are mounted such that their outer surfaces are fully exposed, and which are generally a millimeter or more in longitudinal length, especially in pacing applications where the increased probability of electrode-tissue contact due to a longitudinally longer electrode is desired. It is preferred that an electrode 60 of this invention be configured as a thin walled metallic tube section and have less than one millimeter of exposed longitudinal length. A short electrode longitudinal exposure length (longitudinal length of the electrode that is exposed to blood or other lumen fluid) and a thin wall minimizes electrode echo amplitudes and artifacts. The total length of the electrode 60 is typically substantially shorter than the length of the echogenic member 23 and layers 21, 22.

Figure 6:
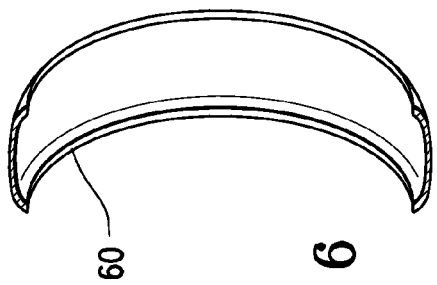
FIG. 6 is a perspective sectional view of the sensing/transmitting component on the catheter of FIG. 5.
Figure 5:
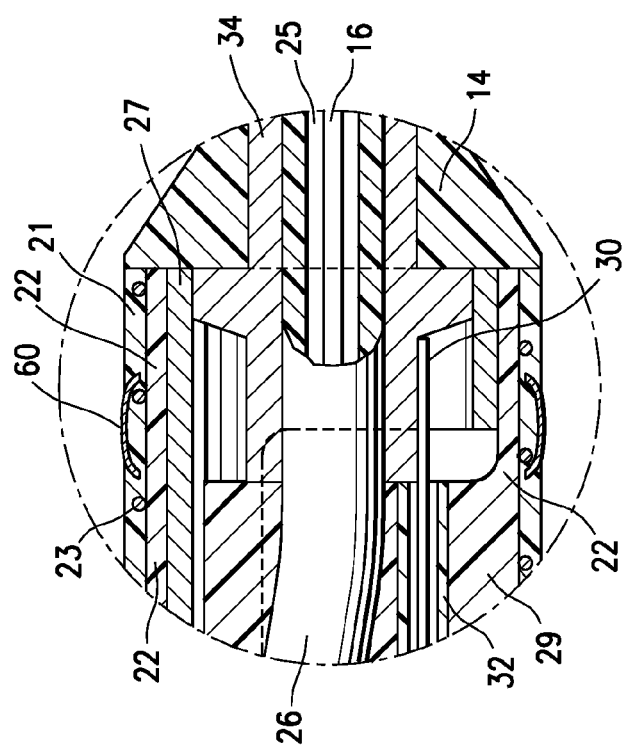
FIG. 5 illustrates a longitudinal cross sectional view of the catheter of FIG. 1, taken within circle-5.

At least a portion of the electrode 60 is exposed, and in a presently preferred embodiment, the electrode 60 is in part imbedded in one or both of the diffusive and dampening layers to prevent/minimize ringing artifacts. FIG. 5 illustrates a longitudinal cross sectional view of electrode 60 in outer layer 21. In the embodiment of FIG. 5, the proximal and distal ends of the electrode have curved ends of a reduced outer and inner diameter, such that they are not exposed. Imbedding the proximal and/or distal portions of the electrode in the diffusive and dampening layer(s) further reduces their ringing artifacts. Further, the longitudinally curved outer surface of electrode 60 is configured to diffusely reflect a portion of the incident sonic energy back to the transducer/probe of the ultrasonic imaging system at a wide range of incident angles and to produce an electrode image with a brightness nearer to and, preferably, slightly brighter than that of the adjacent shaft to facilitate visualizing an electrode's position on the shaft. The electrode 60 has a curved convex outer surface and a correspondingly curved concave inner surface. This configuration provides the desired thin wall thickness together with the desired curved outer surface and imbedded ends. FIG. 6 illustrates a perspective sectional view (cut in half) of curved electrode band 60, having the correspondingly curved inner and outer surfaces. A central section of the electrode 60 between the imbedded ends is exposed, in that it extends above the outer surface of the outer layer 21.

In applications where the probability of electrode-tissue contact is desired to be increased, two or more adjacent, electrically connected electrodes 60 with diffusive and dampening layer material between them may be used to increase the effective electrode exposure length. In some embodiments with more than one shaft electrode 60, additional echogenic members may be used as the lead wire of additional electrodes. In some embodiments, an echogenic member (e.g., wire 23) may extend distal to its electrically connected electrode to provide the desired shaft image.

Although discussed primarily in terms of an electrode 60, other electrical or sensor components such as a transducer, electrical sensor, or fiber optic sensor can be used in place of or in addition to electrode 60. In an embodiment having a fiber optic sensor, the echogenic member 23 could therefore be formed at least in part of glass to function as a fiber optic conductor for the fiber optic sensor, and the glass configured and/or covered to provide the desired echogenicity as discussed above.

As a metallic band at/near the surface of the shaft, the electrode 60 will appear on the ultrasonic imaging system. Thus, it should be understood that the section of the shaft that is rendered substantially echolucent by the echo diffusive and dampening layers is the rest of the deflectable distal section longitudinally spaced from the electrode 60. Similarly, other metallic/echogenic members mounted onto the deflectable distal section will be visible under ultrasonic imaging, although the echogenic member 23 will nonetheless provide an accurate ultrasonic image of the deflectable distal shaft section, the tubular body 50 of which is rendered substantially echolucent in accordance with the invention.

Figure 7:
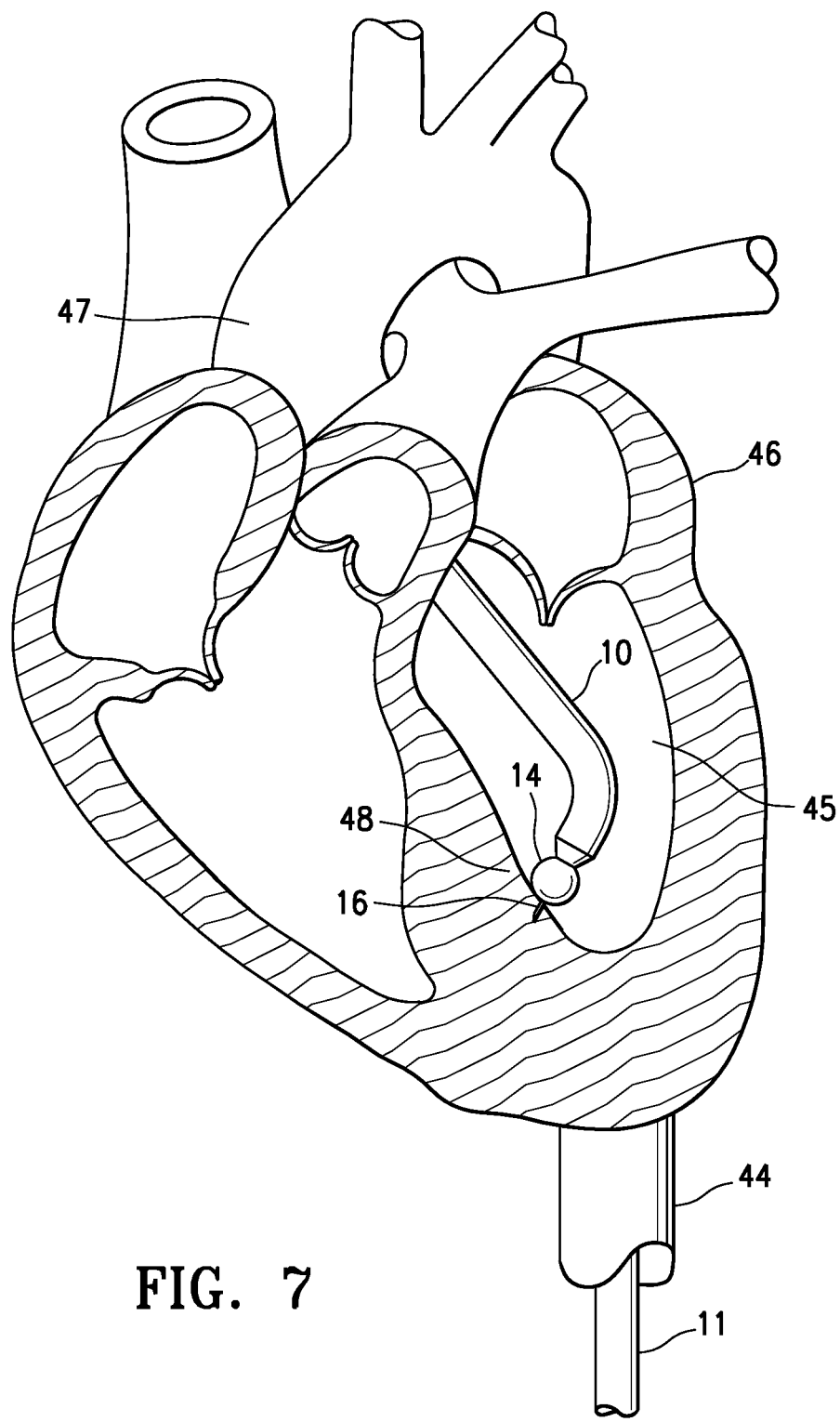
FIG. 7 illustrates the catheter of FIG. 1 within a left ventricle of a patient's heart during a medical procedure.

FIG. 7 illustrates the needle catheter 10 with the distal end of the catheter 10 within the left ventricle 45 of the patient's heart 46. The catheter 10 is typically advanced in a retrograde fashion within the aorta 47, via the lumen of an introducer sheath which is inserted into the femoral artery. The catheter 10 illustrated in the embodiment of FIG. 1 is not configured for advancement over a guidewire, although in alternative embodiments and delivery sites, such as into veins or arteries, a guidewire lumen is provided in the shaft 11 for slidably receiving a guidewire therein. Additionally, in such vessel applications, the guidewire and catheter may be inserted into position using a guiding catheter that is first inserted into the introducer. In this intracardiac application, a deflecting mechanism is desired. By activating the deflection member 30 using the deflection control mechanism 31 the distal end of the catheter is caused to deflect away from the longitudinal axis of the shaft 11. With the distal end of the spherical distal tip 14 thus positioned in contact with a desired site of the ventricle wall, electrical data can be collected from the spherical distal tip electrode 34. The electrical data (e.g., tissue contact ECG) facilitates tissue diagnostics (in combination with echo image ventricle wall motion measures) to determine if the site should be treated or not. The site can be treated by direct injection of a therapeutic agent, such as a biological or chemical agent, from the needle 16. FIG. 7 illustrates the distal end of the spherical distal tip 14 and the port 28 against the ventricle wall, with the needle 16 in the extended configuration advanced out the port 28 and into the cardiac tissue 48 of the ventricle wall. Multiple sites within the left ventricle can be thus accessed and treated using the catheter of the invention.

Although illustrated in the ventricle, a catheter of the invention can be used to inject into the vessel wall or through the vessel into the myocardium or other adjacent tissues. Thus, although the distal needle port 28 is in the distal-most end of the spherical distal tip 14 coaxial with the longitudinal axis of the catheter in the embodiment of FIG. 1 (with the needle extending aligned with the longitudinal axis of the catheter), in alternative embodiments (not shown; e.g., those for injecting into or through a vessel) the catheter 10 has a needle port configured to direct the needle at an angle away from the longitudinal axis of the catheter. For example, the port through which the needle extends can be located eccentric to the longitudinal axis of the catheter or in a side wall of the catheter proximal to the distal end of the distal tip.

FIG. 8 illustrates an alternative embodiment of a shaft section having a first longitudinal portion 81 configured to produce a continuous image and a second longitudinal portion 82 configured to produce a discontinuous image when the distal shaft section is ultrasonically visualized. The shaft section is a deflectable distal shaft section similar to deflectable distal shaft section 12 of needle catheter 10 of FIG. 1, although shaft section could be provided in a variety of suitable locations of a variety of suitable catheters. In a presently preferred embodiment, the discontinuous image second portion 82 is distal to the continuous image first portion 81. In a series of deflectable needle catheters provided with varying length deflectable distal shaft sections, the ability to keep the length of the discontinuous imaging distal portion the same irrespective of the total length of the deflectable distal shaft section in the different catheters provides imaging consistency and facilitates determining if the catheter's operative distal tip is in view during a medical procedure. In a limited viewing window, like current real-time 3D echo images, if a long distal shaft section (longer than the viewing window or longer than the easily viewable anatomy) produced only a discontinuous image portion, it might not be easy to determine whether an end of the discontinuous image distal shaft section in view during a medical procedure was the distal or rather the proximal end of the discontinuous image section, since the entire image could only contain a discontinuous shaft image. However, in the embodiment of FIG. 8, only the distal segment of the distal end of the catheter produces a discontinuous imaging portion and is easy to recognize because the proximal end of the discontinuous image portion is readily identified by being adjacent to the continuous image portion. Thus, the physician can readily recognize the distal end of the catheter, which can otherwise be difficult given the fact that the physician doesn't necessarily know what orientation the catheter is in as it is being viewed.

In the embodiment illustrated in FIG. 8, the catheter 80 generally includes an elongated shaft 11 having a proximal end (not shown), a distal end, and a proximal shaft section 13, a distal shaft section 83 formed at least in part of a metallic member (e.g., cage 27 and/or needle 16). An echo diffusive and dampening polymeric inner layer 84 is on an outer surface of the distal shaft section 83, and an echo diffusive and dampening polymeric outer layer 85 is on an outer surface of the inner layer 84, and an echogenic member 86 is between the inner and outer layers 84, 85 (see FIGS. 9 and 10 illustrating transverse cross sections of FIG. 8 taken along lines 9-9 and 10-10, respectively). The nature and materials of the inner and outer layers 84, 85 and echogenic member 86 are as discussed herein with respect to the embodiment of FIG. 1, except as discussed below. As best shown in FIGS. 9 and 10, along the second longitudinal portion 82 configured to produce a discontinuous shaft image (hereafter the discontinuous shaft image portion 82) the echogenic member 86 is fully encapsulated by the inner and outer layers 84, 85. In contrast, along the first longitudinal portion 81 configured to produce a continuous shaft image (hereafter the continuous shaft image portion 81) the echogenic member 86 outer surface is in part separated from adjacent surrounding surfaces of the inner and outer layers by a gap 87 such that the echogenic member 86 is not fully encapsulated. The terminology "fully encapsulated" should be understood to mean that the outer surface of the entire diameter/periphery of the echogenic member 86 is in contact with the layers 85, 86. Preferably, the gap 87 is sized such that a substantial portion (e.g., about 75 to about 20% of the outer diameter/circumference of the echogenic member) of the outer surface of the echogenic member is not in contact with either the inner or outer layers 84, 85.

Along the continuous shaft image portion 81, the inner and outer layers are preferably in intimate physical contact with each other except around the echogenic member 86, but preferably are not fused, bonded, or otherwise joined with each other along the length of portion 81. Specifically, the outer surface of the inner layer 84 contacts but is not fused to the inner surface of the outer layer 85 around a substantial percentage of the circumference of the inner layer 84. In contrast, along the discontinuous shaft image portion 82, the inner and outer layers are preferably fusion bonded together.

In the illustrated embodiment, the outer layer is caused to "tent" around the echogenic member 86 thereby forming gap 87. Specifically, the inner layer 84 has a substantially circular transverse cross sectional shape, and the echogenic member has a first contacting part 90 (see FIG. 9) contacting the outer surface of the inner layer 84, and a second contacting part 91 opposite to the first part and contacting the inner surface of the outer layer 85 such that the echogenic member 86 raises the inner surface of the outer layer radially away from the adjacent outer surface of the inner layer, and the gap 87 is formed on either side of the echogenic member 86 between the first and second contacting parts 90, 91. However, a variety of suitable configurations can be used which cause the echogenic member outer surface to be in part separated from adjacent surrounding surfaces of the inner and outer layers by a gap such that the echogenic member is not fully encapsulated, such as molding or otherwise shaping the inner or outer layer to form a channel which receives but which is wider or deeper than the echogenic member. The tenting of the outer layer in the embodiment of FIG. 8 causes the outer surface of the outer layer along the first portion to have a protrusion formed by the echogenic member under the outer layer. In contrast, the outer surface of the outer layer along the second portion has a substantially smooth outer surface. In other embodiments, such as an embodiment where the echogenic member is positioned in a channel of suitable dimensions in the OD of the outer layer, tenting may not occur and thus, there will be little or no protrusion of the outer layer, but a portion of the OD of the echogenic member will not be in contact with the inner or outer layers.

In the embodiment illustrated in FIG. 8, the length of the discontinuous shaft image portion 82 is about equal to the length of the continuous shaft image portion 81, however, a variety of suitable relative lengths can be used. In one embodiment of a series of different sized catheters having deflectable distal shaft sections of varying lengths, the discontinuous shaft image portion 82 is about 5 cm in each catheter, whereas the continuous shaft image portion 81 varies from about 1 cm to about 5 cm depending on the total length of the deflectable distal shaft section.

In the illustrated embodiment, the inner and outer layers are fused together along a third longitudinal portion 93 which is located proximal to the first longitudinal portion 81. The third longitudinal portion 93 forms a bond to a proximally adjacent section of the shaft 13 while also providing a smooth transition from the inner and outer layers 84, 85 of the distal shaft section 83 to the proximal adjacent shaft section of the shaft. Additionally, the third longitudinal portion 93 acts as a proximal anchor of the inner and/or outer layers with the echogenic member therebetween to the underlying deflecting distal shaft section assembly. It is preferred that the third longitudinal portion 93 be made short enough that, should this portion of the catheter be imaged, the bright image of the proximal shaft 13 (due to the braid) merges with it and no discontinuous image is produced by portion 93.

Unlike methods which alter the image produced by the shaft from a discontinuous image to a continuous image by modifying the echogenic member (e.g., the turns are brought closer together, or the member is made of a larger diameter wire and/or its position relative to the outer surface of the outer layer is altered) or by manipulating the outer layer to be more diffusive and/or less dampening (e.g., by manipulating the configuration and/or the percent loading of tungsten particles therein), the continuous image portion 81 is provided without such manipulation of the echogenic member or layer composition. Thus, the echogenic member 86 in the embodiment of FIG. 8 extends around the circumference of the inner layer with a substantially uniform spacing between adjacent turns of the echogenic member. Similarly, the outer layer 85 has a substantially uniform composition along the entire length of the outer layer. The embodiment of FIG. 8 is particularly useful when the polymeric materials of the layers 84, 85 do not maintain mechanical integrity at the relatively high percent loading of tungsten required to provide a continuous shaft image with the desired inner and outer layer and echogenic member specifications. Additionally, the embodiment of FIG. 8 facilitates making the bending properties (modulus) of the two portions 81, 82 substantially similar such that the deflecting section forms a continuous single radius curve when deflected, unlike methods in which the compositions or structures of the inner and outer echo diffusive and dampening layers and/or the echogenic member are manipulated to provide a continuous image portion next to a discontinuous image portion. In a presently preferred embodiment, the outer layer has metallic, glass or ceramic echogenic particles loaded in the polymeric material, and the inner layer consists essentially of polymeric material. In one embodiment, the outer layer 85 has tungsten particles at a percent loading of about 10% to about 35% by weight.

While not wishing to be bound by theory it is believed that omitting the fusion step causes what would normally be a discontinuous imaging portion to become a continuous imaging portion as a result of several effects. The sonic energy coupled into the echogenic member from the outer layer is not dissipated/dampened as rapidly as in the discontinuous imaging portion because there is less of the surface of the echogenic member in contact with the inner and outer layers. This lowers the dampening/dissipation of the sonic energy in the echogenic member, allowing it to propagate further along the length of the echogenic member and to send significant sonic energy back into the outer layer (and thus, back to the transducer) over a longer length of the shaft. Also, this sonic energy that is coupled into the outer layer enters the outer layer in an outer layer portion that is not in contact with the inner layer and thus, little of this sonic energy is coupled into the inner layer. Most of the sonic energy that would have been coupled into the inner layer near the echogenic member in the discontinuous imaging portion is now almost completely reflected back into the outer layer and a portion of that is diffusely directed back to the transducer. Thus, the outer layer region near the echogenic member in the continuous imaging portion sends significant sonic energy back to the transducer over a longer length on either side of the echogenic member than in the discontinuous imaging portion. Both of these effects cause the image of the echogenic member and the region near the echogenic member in the continuous portion to appear (image) wider along the length of the shaft and thus, to merge and form a continuous image. However, the overall image brightness of the continuous imaging portion is not much changed from that of the discontinuous imaging portion, even though there is less dampening of the sonic energy coupled into the echogenic member in the continuous imaging portion. This is because with less surface area of the echogenic member in contact with the outer layer in the continuous imaging portion, less sonic energy is coupled into the echogenic member.

In a method of making a shaft section having a first longitudinal portion that produces a continuous image and a second longitudinal portion that produces a discontinuous image, the inner and outer echo diffusive and dampening layers with the echogenic member therebetween are positioned on the shaft section and then are processed in different manners to produce the different echo images, which are preferably of approximately the same amplitude as adjacent tissue interfaces. For example, in one embodiment, the inner and outer layers are caused to melt and fuse together and fully encapsulate the echogenic member to form the discontinuous image producing second portion, whereas little or no melting of the inner and outer layers (or otherwise bonding the layers together and fully encapsulating the echogenic member) is caused to occur during the assembly processing along the first portion, which results in the first portion producing a continuous image when ultrasonically visualized.

In one embodiment, the distal shaft section 83 of the embodiment of FIG. 8 is prepared by applying echo diffusive and dampening polymeric inner and outer layer 84, 85, with echogenic member 86 therebetween, on an outer surface of the shaft section, and applying heat and radially inward pressure on an outer surface of the outer layer to heat the inner and outer layers to a first elevated temperature along a second longitudinal portion of the shaft section, to a second lower elevated temperature along a first longitudinal portion of the shaft section. The first elevated temperature is sufficient to melt and fuse the inner and outer layers together along the second portion, and the second elevated temperature is preferably sufficiently low that the inner and outer layers are not melted and fused together along the first portion. As a result, the inner and outer layers fully encapsulate the echogenic member along the second portion, whereas the outer surface of the echogenic member remains in part separated from adjacent surrounding surfaces of the inner and outer layers by a gap such that the echogenic member is not fully encapsulated along the first portion. A variety of suitable method can be used to apply a differential heat and/or pressure to the first and second longitudinal portions to produce the differential encapsulation of the echogenic member. In one embodiment, the method includes placing a first heat shrink sheath over the outer layer along the first and second portions and a second heat shrink sheath on an outer surface of the first heat shrink sheath along the first portion, such that the first portion is shielded from the applied heat by more heat shrink material thickness than the second portion (thus resulting in the second lower elevated temperature experienced by the layers).

In accordance with the invention, the two layers 21, 22 (or 84, 85) are designed to have specific acoustic impedance values. Ultrasonic test data, material specifications, and standard sonic reflection equations and equations for mixtures of materials are used in the design of the acoustic impedance of the two layers. Additionally, the reflection caused by adding the two layers 21, 22 to a catheter shaft section can be estimated, in order to tailor the characteristics of the two layers 21, 22 to provide the desired acoustic properties, e.g., to control the direct reflection shaft artifact. The layers are configured for being imaged at a particular center frequency and bandwidth of a particular ultrasonic imaging system. The following Example illustrates an embodiment of the present invention.

Example

A deflectable distal shaft section of a needle catheter, having a metal cage, stabilizing tubular member, and lumen defining inner tubular members such as are described in the embodiment of FIG. 1, was covered with a 0.0070 thick layer (i.e., the "inner layer") of a polyurethane block copolymer (DOW Pellethane 2363-90AE Polyurethane Resin) polymeric material, by fitting a tube of the polymeric material onto the metal cage member of the deflectable distal shaft section. The inner layer-forming tube and the stabilizing tubular member are the same polymeric material. A piece of heat shrink tube is placed over the assembly and heat shrunk at an elevated temperature, such that the stabilizing tubular member and the inner layer-forming tube melt and fuse together, encasing the cage and tubular members. After cooling, the heat shrunk tube is slit and removed and discarded. A 0.004 inch diameter Constantan TC type T, H-ML black insulated wire was shaped/wrapped around the inner layer with a pitch of about 5 mm and an inner diameter slightly less than the outer diameter of the inner layer on the assembly, to form an echogenic coil member, and then positioned over the inner layer of the assembly. Next, a 0.007 inch outer layer of a blend of 84% Tecoflex EG80A Polyurethane Resin, 1.44% DOW Pellethane 2363-90AE Polyurethane Resin and loaded with tungsten powder in an amount of 14.56% weight % of the blend was applied by fitting a tube of the compounded blended polymeric material over the coiled wire of the assembly. In this example, a heat shrink tube was again fitted over the distal section of the needle catheter and shrunk with sufficient heat to cause the outer layer tube to melt and flow such that it conformed closely with the inner layer assembly and the echogenic coil member, and after cooling the heat shrunk tube was removed and discarded. The inner layer, outer layer and coil member were coaxial and essentially coextensive (extending along substantially the same length) with a total length of about 6 cm. During ultrasonic imaging, an ultrasound system was set with normal gain settings that image the cardiac anatomy well. The resulting catheter produced discontinuous shaft images (separate diagonal lines) corresponding to the position of the distal shaft section at a wide range of imaging angles relative to the shaft surface, and with an intensity about as bright as the surrounding cardiac tissue structure images. In a comparison example of a distal section of a needle catheter that did not include the coil member, the catheter shaft reflections were shown to be so low that the image of the catheter virtually disappeared from the cardiac image, except for its direct reflection image, which was reduced to a small spot in the 3D image. Thus, the layers effectively dampened out the reflections from the other shaft components deeper inside the shaft that are covered by the two layers to a degree that no detectable image or artifact was generated by them. For example, the percent of incident sonic energy directly reflected back to an ultrasound imaging system from the resulting covered deflectable distal shaft section is calculated to be only about 0.04 percent for an ultrasonic wave of approximately 2.25 MHz (which is approximately equal to the center frequency of common conventional multi-frequency emitting probes). For comparison purposes, calculations indicate that the direct reflection off of the myocardium is only about 0.055 percent of the incident sonic energy.

To construct the substantially echolucent shaft section, one uses material section, calculation of layer properties, testing, and material adjustments in order to ultimately result in the desired catheter shaft section. For example, imaging a polymer or polymer blend of a known, measured thickness with the ultrasonic imaging system and measuring its imaged thickness allows one to calculate the speed of sound in the polymer or polymer blend. If the density of the polymer or polymer blend is then measured or obtained from the manufacturer, the modulus (commonly termed "coefficient of stiffness" in acoustic texts) and the acoustic impedance of the polymer or polymer blend may be calculated using well known equations. If the material composition is changed as for example by the addition of a known amount of immiscible particles with a known material density and modulus, the new material density and modulus can be calculated, and this new modulus and density may then be used to calculate the speed of sound and acoustic impedance of the new particle/polymer blend. The fractional amount of sonic energy reflected at the interface between two materials of known acoustic impedance may be calculated, such as the interface between the outer layer 21 and the blood of the body lumen (the acoustic impedances and speed of sound of blood, various tissues and water being well known or available in the literature). Additionally, the superposition of two reflected sonic waves of calculated/known amplitudes at frequencies of interest and the same difference in path length (twice the outer layer thickness) can also be calculated.

Except as specifically discussed herein, the catheter shaft tubular members can be formed of a variety of suitable materials commonly used in catheter construction and the components can be secured together using convention techniques including fusion and adhesive bonding. The inner tubular member 26 is typically formed of a single layered, integral one-piece tube extending from the proximal to the distal end of the catheter, although multiple sections of tubing with communicating lumens and/or a multilayered tube(s) can alternatively be used. The proximal shaft section 13 can have a variety of suitable shaft configurations as are conventionally known for intraluminal catheters. The proximal shaft section 13 of catheter 10 is typically formed at least in part of metal, such as a polymer reinforced with a braided or coiled metallic filaments or a hypotube or slotted metallic tube, although it may alternatively or in addition consist of a high modulus polymer. In the illustrated embodiment, the shaft 11 has a braided body layer 53 extending distally from a proximal end section of the catheter, and comprising a polymeric material encapsulating a wound tubular support layer typically formed of braided filaments of a metal such as stainless steel. The braid is encapsulated by an outer layer which is typically formed of multiple sections of differing durometers/polymers joined end to end to provide a stiffness transitions along the length of the catheter. The braid is formed over a polymeric core layer 54.

Although the catheter 10 is illustrated with a spherical distal tip 14, the controlled amplitude echo reflective/diffusive and dampened shaft portion provided by layers 21, 22 and coil member 23, could be used on a variety of suitable catheters including catheters not having a spherical distal tip 14. The spherical distal tip 14 is configured to facilitate ultrasonically imaging the distal tip. Therefore, it should be understood that the ultrasound image of the deflectable distal shaft section 12, which consists essentially of the sonic reflections of the coil member 23, refers to the image resulting from the section of the shaft having members 21, 22 and 23 therealong, and not to the image resulting from other sections of the catheter 10.

Moreover, a catheter of the invention can be a variety of suitable catheters/other devices that may be guided by ultrasound and/or must be present in the anatomy during ultrasonic imaging. Thus, the term "catheter" should be understood broadly to refer to a variety of medical devices. Additionally, although the catheter features are useful for use with 2D or 3D ultrasonic imaging systems, it should be noted that for the purpose of catheter guidance, a 3D echo system is preferred to the "slice" image provided by a 2D echo system. A 2D echo system produces images that are like viewing a very thin planar slice thru the anatomy and the catheter, making it extremely difficult to distinguish/find a catheter, follow a catheter to its tip or other relevant portion and determine where in the anatomy the relevant portion of a catheter is located/oriented or is located/oriented relative to a previous location/orientation. A typical 3D echo system produces images that can either be a see-through representation of 3D volume of the anatomy and catheter or a 3D surface image of the same. The real-time 3D image only covers a small viewing section, due inherent sonic propagation limitations, however; these viewing sections are also typically gathered over the period of several cardiac cycles to create a larger reconstructed image, if desired. In a 3D image, anatomic reference points abound in the image and, with a properly echogenic catheter (as described in this application), all portions of the catheter in the image volume may be seen, and the direction of the catheter shaft relative to the anatomy is easily visualized as described herein. Although discussed primarily in terms of being viewed under ultrasonic imaging using an ultrasound imaging system outside of the patient's body lumen, a catheter of the invention can be viewed with echo systems that place transducers inside the patient's body, such as for example intracardiac echocardiogram (ICE) and transesophageal echocardiogram (TEE) echo systems. Although possible, viewing a catheter of the invention using an intravascular ultrasound (IVUS) imaging catheter that images from inside a vessel is not a presently preferred embodiment.

Although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

I claim:

1. A method of making a catheter for use in a patient's body lumen, configured for being viewed under ultrasonic imaging using an ultrasound imaging system outside of the patient's body lumen, comprising:
   a) applying an echo diffusive and dampening polymeric inner and outer layer, with an echogenic member therebetween, on an outer surface of the shaft section; and
   b) applying heat and radially inward pressure on an outer surface of the outer layer to heat the inner and outer layers to a first elevated temperature along a second longitudinal portion of the shaft section such that the inner and outer layers fully encapsulate the echogenic member along the second portion, and to a second elevated temperature less than the first elevated temperature along a first longitudinal portion of the shaft section so that an outer surface of the echogenic member is in part separated from adjacent surrounding surfaces of the inner and outer layers by a gap such that the echogenic member is not fully encapsulated along the first portion, and the first portion forms a continuous shaft image and the second portion forms a discontinuous shaft image on a 3D ultrasound image format.

2. The method of claim 1 wherein the first elevated temperature is sufficient to melt and fuse the inner and outer layers together along the second portion, and the second elevated temperature is sufficiently low that the inner and outer layers are not melted and fused together along the first portion.

3. The method of claim 1 wherein b) includes placing a first heat shrink sheath over the outer layer along the first and second portions and a second shorter heat shrink sheath on an outer surface of the first heat shrink sheath along the first portion, such that the first portion is shielded from the applied heat more than the first portion.

4. A method of making a catheter for use in a patient's body lumen, configured for being viewed under ultrasonic imaging using an ultrasound imaging system outside of the patient's body lumen, comprising:
   a) applying an echo diffusive and dampening polymeric inner layer and outer layer, with an echogenic member therebetween, on an outer surface of the shaft section; and
   b) applying heat and radially inward pressure on an outer surface of the outer layer to heat the inner and outer layers to fully encapsulate the echogenic member and form a discontinuous shaft image on a 3D ultrasound image format.

5. The catheter of claim 4 wherein the outer layer has metallic or glass echogenic particles, and the inner layer consists essentially of polymeric material.

6. The catheter of claim 5 wherein the outer layer has tungsten particles at a percent loading of 10% to 35%.

7. The catheter of claim 4 wherein the outer layer is formed at least in part of a different polymeric material than the inner layer.

8. A method of making a catheter for use in a patient's body lumen, configured for being viewed under ultrasonic imaging using an ultrasound imaging system outside of the patient's body lumen, comprising:
   a) applying an echo diffusive and dampening polymeric inner layer and outer layer, with an echogenic member therebetween, on an outer surface of the shaft section; and
   b) applying heat and radially inward pressure on an outer surface of the outer layer to heat the inner and outer layers to fully encapsulate the echogenic member and form a continuous shaft image on a 3D ultrasound image format.

9. The catheter of claim 8 wherein the outer layer has metallic or glass echogenic particles, and the inner layer consists essentially of polymeric material.

10. The catheter of claim 9 wherein the outer layer has tungsten particles at a percent loading of 10% to 35%.

11. The catheter of claim 8 wherein the outer layer is formed at least in part of a different polymeric material than the inner layer.

12. A method of making a catheter for use in a patient's body lumen, configured for being viewed under ultrasonic imaging using an ultrasound imaging system outside of the patient's body lumen, comprising:
   a) applying an echo diffusive and dampening polymeric inner layer having an acoustic impedance and an echo diffusive and dampening polymeric outer layer having an acoustic impedance different from the inner layer, with an echogenic member therebetween, on an outer surface of the shaft section; and
   b) applying heat and radially inward pressure on an outer surface of the outer layer to heat the inner and outer layers to fully encapsulate the echogenic member and form a discontinuous shaft image on a 3D ultrasound image format.

13. The catheter of claim 12 wherein the outer layer has metallic or glass echogenic particles, and the inner layer consists essentially of polymeric material.

14. The catheter of claim 13 wherein the outer layer has tungsten particles at a percent loading of 10% to 35%.

15. The catheter of claim 12 wherein the outer layer is formed at least in part of a different polymeric material than the inner layer.

16. A method of making a catheter for use in a patient's body lumen, configured for being viewed under ultrasonic imaging using an ultrasound imaging system outside of the patient's body lumen, comprising:
   a) applying an echo diffusive and dampening polymeric inner layer having an acoustic impedance and an echo diffusive and dampening polymeric outer layer having an acoustic impedance different from the inner layer, with an echogenic member therebetween, on an outer surface of the shaft section; and
   b) applying heat and radially inward pressure on an outer surface of the outer layer to heat the inner and outer layers to fully encapsulate the echogenic member and form a continuous shaft image on a 3D ultrasound image format.

17. The catheter of claim 16 wherein the outer layer has metallic or glass echogenic particles, and the inner layer consists essentially of polymeric material.

18. The catheter of claim 17 wherein the outer layer has tungsten particles at a percent loading of 10% to 35%.

19. The catheter of claim 16 wherein the outer layer is formed at least in part of a different polymeric material than the inner layer.

* * * * *